US008178303B2

(12) United States Patent
Shihabi

(10) Patent No.: US 8,178,303 B2
(45) Date of Patent: May 15, 2012

(54) INCREASING THE SPEED OF CRYOGLOBULIN PRECIPITATION

(75) Inventor: Zak A. Shihabi, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1359 days.

(21) Appl. No.: 11/003,631

(22) Filed: Dec. 3, 2004

(65) Prior Publication Data

US 2005/0234224 A1 Oct. 20, 2005

Related U.S. Application Data

(60) Provisional application No. 60/527,046, filed on Dec. 4, 2003.

(51) Int. Cl.
*G01N 33/53* (2006.01)

(52) U.S. Cl. .......................................................... 435/7.1

(58) Field of Classification Search ........................ None
See application file for complete search history.

(56) References Cited

OTHER PUBLICATIONS

Kallemuchikkal et al., Arch Pathol. Lab Med. 1999, 123:119-125.*
Hardin, PNAS, 1981, vol. 78, p. 4562-4565.*
Wikepedia, saline, p. 1-2.*
Mola et al. Clinical and Exp. Rheumatology, vol. 1, p. 35-40, 1983.*
DiStasio et al. Clin. Chem. Lab. Med. Feb. 2003, vol. 41(2):152-158.*
Wikepedia, saline, 2007, p. 1-2.*
Brouet J C, et al., Biologic and clinical significance of cryoglobulins. A report of 86 cases., Am J Med (Nov. 1974) 57(5): 775-88.
Kalovidouris A E and Johnson R L, Rapid cryoglobulin screening: An aid to the clinician, Annals of the Rheumatic Diseases (1978) 37: 444-448.
Yang L C et al., A micromethod for the analysis of cryoglobulins via laser nephelometry: evaluation and comparison to C1q binding activity in autoimmune diseases in pediatrics, Pidatr Res. (Jul. 1980) 14(7); 858-62.
Dolcher M P, et al., Autoantibodies from mixed cryoglobulinaemia patients bind glomerular antigens, Clin Exp Immunol (May 1994) 96(2): 317-22.
Shihabi, Z K; Analysis and general classification of serum cryoglobulins by capillary zone electrophoresis, Electrophoresis (Oct. 1996) 17(10): 1607-12.
Shihabi, Z K, Cryoglobulins: An important but neglected clinical test, Annals of Clinical & Laboratory Science (2006) 36(4):395-408.
Vermeersch P et al. A critical appraisal of current practice in the detection, analysis, and reporting of cryoglobulins. Clinical Chemistry. 2008: 54(1): 39-43.

* cited by examiner

*Primary Examiner* — Yunsoo Kim
(74) *Attorney, Agent, or Firm* — Myers Bigel Sibley & Sajovec, P.A.

(57) ABSTRACT

The present invention provides a method for the precipitation of cryoglobulins. In general, the method comprises the steps of: (a) providing a cryoglobulin sample; (b) providing a reagent such as a buffer reagent for decreasing the ionic strength of the sample; (c) combining the cryoglobulin sample with the buffer reagent to decrease the ionic strength of the test sample and produce a test sample; (d) chilling the test sample to form a cryoblobulin precipitate in said test sample; and then, optionally but preferably, (e) centrifuging the test sample to separate the cryoglobulin precipitate from said test sample. Tests kits useful for carrying out such methods are also provided.

20 Claims, 4 Drawing Sheets

INCREASING THE SPEED OF CRYOGLOBULIN PRECIPITATION

RELATED APPLICATIONS

This application claims the benefit of U.S. provisional patent application Ser. No. 60/527,046, filed Dec. 4, 2003, the disclosure of which is incorporated by reference herein in its entirety.

FIELD OF THE INVENTION

The present invention concerns methods, reagents and kits for the precipitation and detection of cryoglobulins, particularly type III cryoglobulins.

BACKGROUND OF THE INVENTION

The cryoglobulins are a family of immunogloblulins that persist in the serum, precipitate with cold temperature <37° C., and resolubilize when rewarmed [J-P. Brouet et al., *Am. J. Med.* 57, 755-788 (1974); M. Dolcher et al., *Clin. Exptl. Immun.* 96, 317-322 (1994)). Cryloglobulins precipitate at lower temperatures, a phenomenon known as cold precipitation. Cryoglublinemia is a disorder of cryloglobulin function characterized by a typical triad of clinical symptoms—purpura, weakness, and arthralgias—and by one or more organ pathologies: e.g., hepatitis, glomerulonephritis, peripheral neuropathy, skin ulcers and diffuse vasculitis.

Cryloglobulins are quite heterogeneous and behave differently with respect to precipitation, dissolution or—more importantly—the disorders they produce in different body tissues. The cryoprecipitation phenomenon is unique for each cryoglobulin, and depends on the intrinsic properties of the immunoglobulin, the protein environment, temperature and surrounding ionic concentrations. The cold precipitation characteristic of the cryloglobulins is quite variable between the different cryoglobulins: For example, type I cryoglobulins (which are rare) can precipitate rapidly within minutes at temperatures close to body temperature, while type III cryoglobulins (which are common) hardly precipitate even after a week at ~4° C.

In vivo, cryoglobulins precipitate in the capillaries and small blood vessels probably where the skin can be subjected to a very low temperature, often causing cutaneous problems, e.g., purpura, vasculitis and skin ulcers. These complexes can be carried to other organs causing further complications such as nephropathy and neuropathy.

Many clinical laboratories visually examine cryoglobulins upon sample cooling. Visual examination can detect type I and II cryoglobulins, which are present mostly in 100-1000 mg/dL amounts. However, type III cryoglobulins, which constitute about half of all samples presented to a clinical laboratory, are present in small amounts 3-50 mg/dL. Such small amounts can not be detected easily by visual examination.

Two works attempted to speed up the analysis mainly for screening purposes based on turbidity or nephelometry of the early stages of the precipitation (A. Kalovidouris and R. Johnson, *Ann. Rheum. Dis.* 37, 444-448 (1978); L. Yang et al., *Pediatr. Res.* 14, 858-862 (1980)). However, these techniques are not useful for quantitation or phenotyping. Other workers attempted to increase the amount of precipitation while keeping the samples cold for the 5 days analysis time. Accordingly, there is a need for new techniques for the rapid precipitation and analysis of cryoglobulins, particularly type III cryoglobulins.

SUMMARY OF THE INVENTION

The present invention is based on the finding that cryoglobulin precipitation may be sped up and increased by decreasing the ionic strength of the serum through dilution with a buffer, or through simple dilution in any solution including water.

A first aspect of the present invention is a method for the precipitation of cryoglobulins. In general, the method comprises the steps of: (a) providing a cryoglobulin sample; (b) providing a reagent such as a buffer reagent for decreasing the ionic strength of the sample; (c) combining the cryoglobulin sample with the buffer reagent to decrease the ionic strength of the test sample and produce a test sample; (d) chilling the test sample to to form a cryoblobulin precipitate in said test sample; and then, optionally but preferably, (e) centrifuging the test sample to separate the cryoglobulin precipitate from said test sample.

A further aspect of the present invention is a test kit, comprising: (a) a buffer reagent as described herein, and (b) instructions for carrying out the method of precipitating cryoglobulins as described herein.

The foregoing and other aspects of the present invention are explained in greater detail in the drawings herein and the specification set forth below.

DETAILED DESCRIPTIONS OF THE PREFERRED EMBODIMENTS

Figure 1:
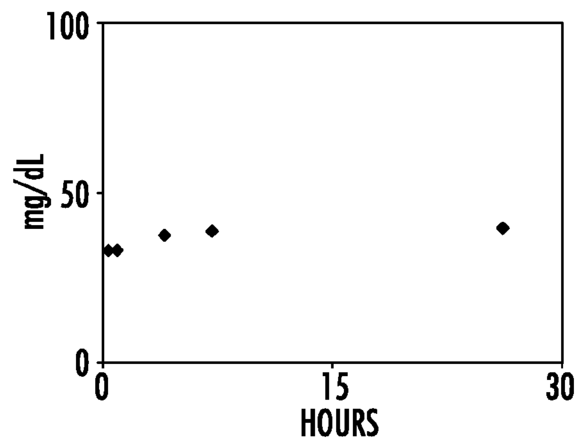
FIG. 1 shows the effect of time on the precipitation of cryoglobulins at 0° C.

Samples used to carry out the present invention are cryoglobulin containing-samples, and are in general blood samples, including any cryoglobulin-containing fraction thereof. Serum samples are particularly preferred. In general the cryoglobulin samples are human samples, but the samples may be from other mammalian species such as dogs, cats, cattle, horses, or the like, for veterinary purposes. The sample may contain any type of cryoglobulin, including type I, type II, or type III cryoglobulin, as in some embodiments the type is not determined until after precipitation.

Reagents or buffer reagents of the present invention are aqueous reagents containing a predetermined amount of a salt adapted to decrease the ionic strength of the serum and enhance the cryoprecipitation step. In one embodiment the salt is preferably sodium chloride (NaCl), which is preferably included in the buffer reagent in an amount ranging from 1 or 2 g/L up to 4, 6 or 9 g/L. A sodium chloride concentration of 2.6 g/L is currently preferred. In some embodiments, salt is absent from the reagent. Any suitable buffer system can be employed, with phosphate buffers currently preferred. In one embodiment the phosphate buffer is included in an amount of from 0.1 or 0.5 to 1.5, 2 or 3 g/L of $Na_2HPO_4$ and from 0.01 or 0.05 to 1 or 2 g/L $NaH_2PO_4$. In a preferred embodiment, the phosphate buffer is included as 0.9 g/L $Na_2HPO_4$ and 0.2 g/L $NaH_2PO_4$. In other embodiments the reagent may be free of additional buffering systems. The reagent may optionally contain other ingredients such as preservatives, with a preferred embodiment containing 5 mg/L sodium azide as a preservative. Numerous alternate preservatives and other optional ingredients will readily be apparent to persons skilled in the art.

The cryoglobulin sample may be combined with the buffer reagent to produce a test sample by any suitable means, such as pipetting or micropipetting one or the other, or both, into a common vessel such as a centrifuge or microcentrifuge tube. In one embodiment, the amount of cryoglobulin sample utilized is from 100 μL to 1 mL, most preferably 500 μL. In one embodiment, the amount of buffer reagent utilized is from 0.5 mL or 1 mL to 5 or 10 mL, most preferably 2 mL. Stated otherwise, the ratio of cryoglobulin sample to buffer reagent by volume is, in general, from 1:1 to 1:10, most preferably about 1:4.

After the cryoglobulin sample and the buffer reagent are combined, they are preferably chilled to facilitate the formation of a cryoglobulin precipitate. Chilling can be at any suitable temperature less than room temperature, and for example may be carried out at a temperature of from −10 or −5° C. up to 10 or 20° C. In one embodiment chilling is carried out by placing the container in which the test sample is carried in a refrigerator; in another embodiment chilling is carried out by placing the container in which the test sample is found in an ice bath. Chilling may be carried out for any suitable period of time, but one advantage of the present invention is that the precipitation can be carried out rapidly, and hence the chilling step is preferably carried out for a time of from about 10, 15 or 20 minutes about to 1, 2 or 3 hours, or more.

After the test sample has been chilled to form the precipitate, it can then be visually inspected immediately or promptly after the chilling step, or centrifuged immediately or promptly after the chilling step (e.g., within a time of from 15 minutes or 1 or 2 hours, or within 24 hours if the test is carried out overnight) to separate the precipitate from supernatant.

The precipitate can be visually inspected or, stored or shipped for further analysis, or promptly analyzed to determine its type, in accordance with known techniques (for example, by (f) solubilizing the cryoglobulin precipitate to form a dissolved precipitate, and then (g) analyzing the dissolved precipitate by electrophoresis).

Test kits for carrying out the present invention generally comprise a buffer reagent as described above, combined with or associated with instructions for carrying out the method described herein. The instructions may be printed instructions on a sheet of paper, or printed on a container for the buffer reagent, printed on a package containing the container of buffer reagent, or combinations thereof. For example, in one embodiment, a container carrying the buffer reagent may be packaged along with a sheet of instructions for carrying out the method described herein. In another embodiment, a container of the buffer reagent may have printed thereon a reference to an address on the world wide web where instructions for carrying out the method of the present invention are located.

The examples which follow are provided to further illustrate the present invention, and are not to be construed as limiting thereof. In general, as shown in the Examples which follow, in order to accelerate precipitation and improve the yield of these proteins the precipitation step was enhanced through a lowered but fixed ionic strength phosphate buffer for 30 min. in addition to cold temperature exposure. As a result of this simple treatment the three types of cryoglobulins are precipitated rapidly with a 2-5 fold increase in amount of the precipitate. Several other advantages also result from this method. The first step of precipitation acts also as a wash step thus the wash steps are decreased. Phenotyping and quantification of the precipitate are also simplified with better accuracy in this method. A better method for dissolution of the cryoproteins is described. More importantly, few patients who are negative with simple cooling show positive results with new method. The clinical symptoms of these patients are also described, and are similar to those having cryoglobulinemia.

The present invention is explained in greater detail in the following non-limiting Examples.

EXAMPLE 1

Precipitation Materials and Methods

For Capillary electrophoresis (CE); Serum (500 μL) was mixed with 2 ml of cold of phosphate buffer: (0.9 g $Na_2HPO_4$ and 0.2 g/L $NaH_2PO_4$, pH 7.3±0.1 containing 2.6 g/L NaCL and preserved with 5 mg/L sodium azide) in glass tube and left on iced-water for 30 min. (The volume is doubled or tripled for agarose gel electrophoresis). Tubes were centrifuged×5000 g for 7 minutes. The supernatant was removed carefully and the precipitate was washed again with 3 ml of the above phosphate buffer without disturbing the precipitate. The tubes were turned upside to remove the last drop of wash. (If the precipitate is disturbed the tubes are re-centrifuged).

EXAMPLE 2

Solubilization Materials and Methods

For CE, the precipitate was dissolved in 100 ul of a warmed (37° C.) aliquot of solubilizing Reagent (CAPS 250 mg, Triton X 405, 250 uL, sodium chloride 400 mg, boric acid 80 mg/100 ml, pH 10.5 Azide 5 mg/l). Triton X peak can act as an internal standard in the CE. For agarose gel electrophoresis the precipitate is dissolved in 25 ul of a warmed (37° C.) aliquot of a different solubilizing reagent: CAPS 500 mg, Triton X 405, 250 uL, sodium chloride 400 mg, 20 mg lysozyme (internal standard)/100 ml, pH 10.5 (Azide 5 mg/l).

The dissolved precipitate was analyzed by capillary or gel electrophoresis in accordance with known techniques (see, e.g., Z. Shihabi, *Electrophoresis*, 17, 1607-1612 (1996)). The gel electrophoresis technique is routinely used. At the same time serum was analyzed by same electrophoresis after proper dilution with the Solubilizing Reagent (fifty folds for CE). Phenotyping is performed from a comparison of the cryoprecipitate to that of serum as described earlier.

Quantification is performed based on the ratio of cryoglobulins/internal standard correcting for albumin in the precipitate to that of the serum. In essence the total protein as well as the ratio of cryoglobulins to albumin of both the cryoglobulins and serum are determined. The amount of carry over of globulin from the serum into the cryoglobulins are determined and corrected based on albumin as described earlier (Z. Shihabi, supra).

EXAMPLE 3

Precipitation Time and Ionic Strength

Initially the optimum conditions for precipitation of globulins from patients positive for cryoglobulins was studied, while keeping the globulins of normal patients negative. The amount of sodium ions in a phosphate buffer at pH 7.3 was optimized for precipitation of a pool of patients positive for cryoglobulins vs. a pooled of serum from healthy individuals. A concentration of salt of 2-4 g/L gave the best amount of precipitation for the positive pool with minimum amount for the control pool. Thus, for routine work, 2.6 g/L of NaCl buffered with 7 mmol/l sodium phosphate buffer (equivalent to ~3.3 g/NaCl) was chosen for routine analysis. A decrease in the sodium chloride increases the precipitation in both the positive and negative pools; while an increase in the sodium chloride brings along the reverse in both pools.

The optimum time for precipitation at 0° C. degrees for the positive pool sample (type 3) vs. the negative pool was also investigated. The amount of precipitate after 15 minutes and 1, 4, 7, and 24 hours were 33, 33, 38, 41, and 37 mg/dl, respectively, for the positive sample, with no precipitation for the negative pool (see FIG. 1). This indicates that precipitation is complete in about 15 minutes. However, for routine work, a thirty minute time period was chosen.

EXAMPLE 4

Precipitation Temperature

Figure 2:
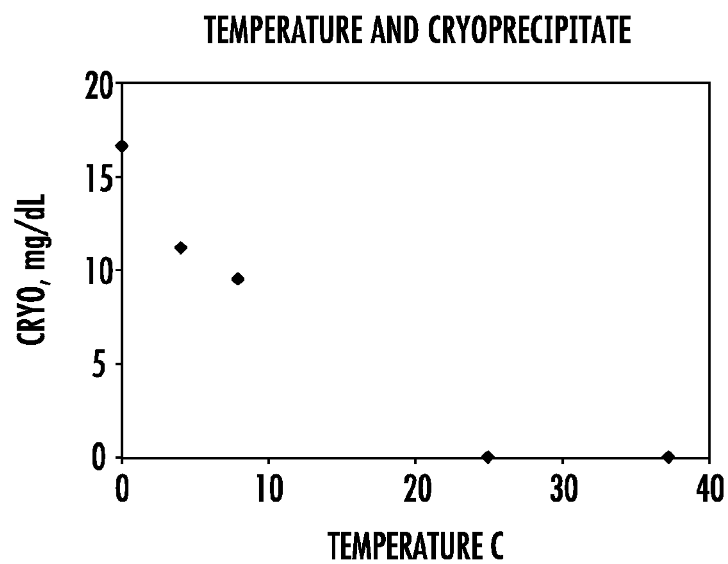
FIG. 2 shows the effect of temperature at 2.5 g/L of NaCl on cryoglobulin precipitation.

The optimum temperature for precipitation was also investigated. FIG. 2 shows the precipitation increases with a decrease in temperature, with maximum precipitation occurring at 0° C. This temperature in practice is easy to achieve by adding ice to water. At temperatures above 25° C. no precipitation was achieved, indicating the precipitated proteins are cryoproteins in nature requiring the cold temperature.

EXAMPLE 5

Precipitation Volume and Serum Ratio

The preferred volumes and ratio of serum to the saline solution was examined from two perspectives: First, to obtain maximum precipitation; second, to obtain a cleaner precipitate with a minimum amount of albumin. Serum was diluted in saline solution at a ratio of 1:5, 10 and 1:20. The best ratio was found to be 1:5, and the optimum volume was 0.5 ml serum in 2.0 ml saline. This produced the minimum amount of albumin in the precipitate and was easy to handle for the centrifugation.

These initial experiments provided the optimum conditions for producing rapid precipitation. The speed and simplicity of this method provided the ability to perform large amounts of screening and determining the reference interval. The reference range for about 50 samples is 0-3 mg/dL. This is similar to that previously described (Z. Shihabi, supra). Most of the old methods for precipitation cryoglobulins essentially ignored the reference range, assuming it is zero.

EXAMPLE 6

Phenotyping of Cryoglobulins

Figure 3:
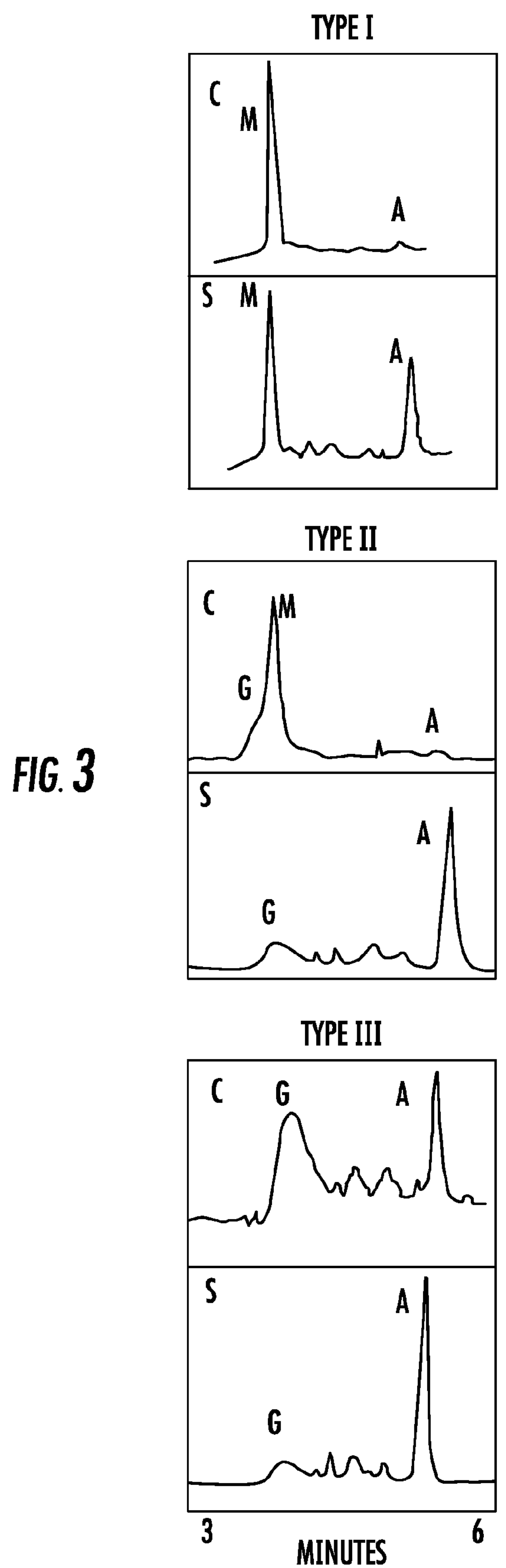
FIG. 3 shows the precipitation and typing of the three types of cryoglobulins by the method of the present invention: Type I 316 mg/dL; type II 51 mg/dL; and Type III 19 mg/dL, based on capillary electrophoresis (C=cryoglobulins; S=serum).

Brouet (supra) was the first to group the cryoglobulins into 3 phenotypes. The ability to perform phenotype cryoglobulins by the method of the present invention was compared to the previously method of Z. Shihabi, supra. FIG. 3 illustrates that the three basic types of cryoglobulins can be precipitated and phenotyped by this method based on the electrophoretic pattern. In type I the serum contains a monoclonal spike which is precipitated and appears again in the cryoglobulins fraction with the same migration. The ratio of the M spike to albumin is much higher in the cryoglobulins fraction compared to that in the serum. Type 2 shows a monoclonal band in the cryoglobulins (usually an Ig M) in addition to the increased polyclonal igG. The monoclonal band is absent in the serum. Type 3 shows only a polyclonal increase in cryoprecipitation the gamma region (polyclonal IgM in addition to the poly IgG) compared to that in the serum. It is important to correct the globulin based on the albumin if present. The only difference between this method and the previous methods is the speed and ease by which the analysis is performed. Immunofixation is a complementary but not necessary for phenotyping.

Figure 4:
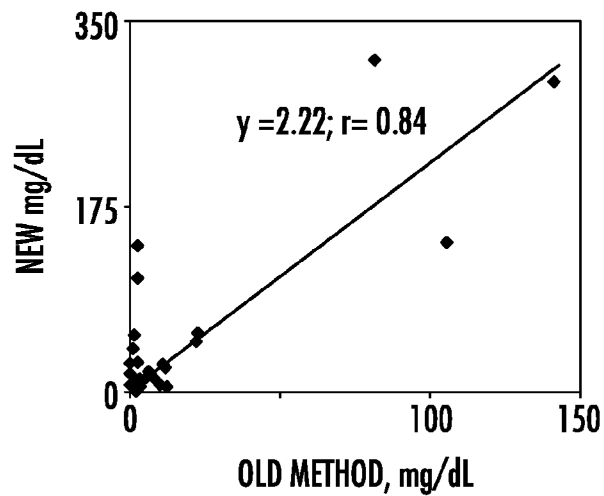
FIG. 4 shows the correlation between the method of the invention and direct precipitation methods for 60 samples.

FIG. 4 illustrates the correlation between the two methods for 60 samples. The regression analysis indicates a good correlation between the two methods; however, the slope is close to 2.5 higher by the new method. Type II give the same values by the two methods. However, Type III, which are the majority of samples (~50%), give about 3-5 times higher by the new method, Table 1. It is interesting that patients with infection including those with hepatitis and those with leukemia give much higher values by the new method, Table I.

TABLE I

Cryoglobulin analysis by the present invention vs. direct serum precipitation (mean, mg/dL).

| Diagnosis | Mean mg/dL New | Mean mg/dL old | N |
|---|---|---|---|
| Infect/Hepatitis | 41.0 | 9.3 | 20 |
| Vascu/Skin Ulcers | 37.5 | 44.2 | 9 |
| Neuropathy | 26.5 | 2.7 | 8 |
| R Arth/SLE | 16.7 | 5.8 | 8 |
| RF/Insuf | 48.6 | 60.2 | 5 |
| CA/Leuk | 29.2 | 0.7 | 5 |
| CVD | 18.7 | 7.5 | 5 |
| TOTAL | 31.2 | 18.6 | 60 |

A high incidence of patients with hepatitis with cryoglobulins which were negative by the old method are positive by new one. Seventeen patients had disorders or symptoms associated with the presence of cryoglobulinemia as broken into different sub-groups, Table II.

TABLE II

Cryoglobulins Quantification by the New Method (precipitation for 1 hr) vs. by the Old method (precipitation of serum for 1 weak) (mean, mg/dL).

| Diagnosis | New | Old | N |
|---|---|---|---|
| Infection/Hepatitis | 41.0 | 9.3 | 20 |
| Vascular/Skin Ulcers | 37.5 | 44.2 | 9 |
| Neuropathy | 26.5 | 2.7 | 8 |

TABLE II-continued

Cryoglobulins Quantification by the New Method (precipitation for 1 hr) vs. by the Old method (precipitation of serum for 1 weak) (mean, mg/dL).

| Diagnosis | New | Old | N |
|---|---|---|---|
| Rheumatoid Arthritis/ SLE | 16.7 | 5.8 | 8 |
| Renal failure/ Insufficiency | 48.6 | 60.2 | 5 |
| Carcinoma/Leukemia | 29.2 | 0.7 | 5 |
| Coronary vascular disease | 18.7 | 7.5 | 5 |
| Total | 31.2 | 18.6 | 60 |

The diagnosis of these patients is consistent to those typical for cryoglobulins (R. Lightfoot, In W. Kelley et al., *Textbook of Rheumatology,* 1378-1385 (Philadelphia, W. Sanders. Co. 1981); R. McIntosh et al., *J. Lab. Clin. Med.* 75, 566-577 (1970); K. Miyamoto, *International. J. Biol. Macromolecules* 28, 183-189 (2001)). This indicates that the new method is more sensitive than prior methods without the need for a 7-day precipitation period.

EXAMPLE 7

Effect of the Second Wash

Diluting the serum with the precipitation reagent substituted for one wash, thus simplifying the procedure.

EXAMPLE 8

Cryoglobulin Solubility

Since each cryoglobulin is different from the others some cryoglobulins do not dissolve by diluting then in warm saline or water. It was found that using the mixture of solubilizing agents which is based on buffers, detergents, high pH and salts as described earlier is preferred to using a single solvent.

EXAMPLE 9

Protein Interferences

Figure 5:
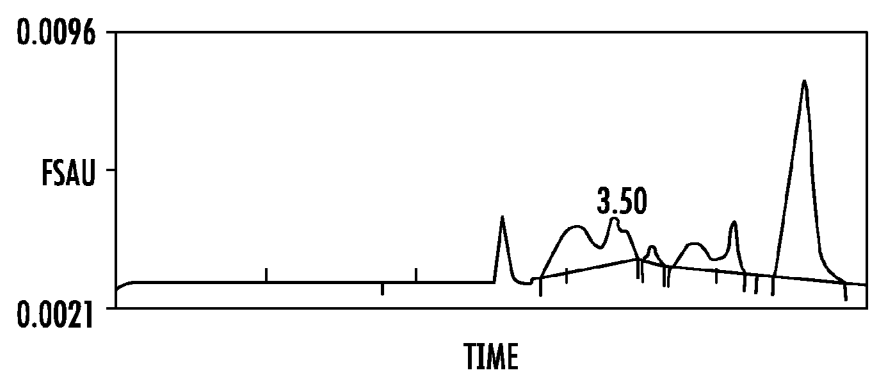
FIG. 5: Top serum from a renal patient showing fibrinogen (3.50); middle cryofibrinogen (4.15); bottom Hemoglobin, H.
Figure 5:
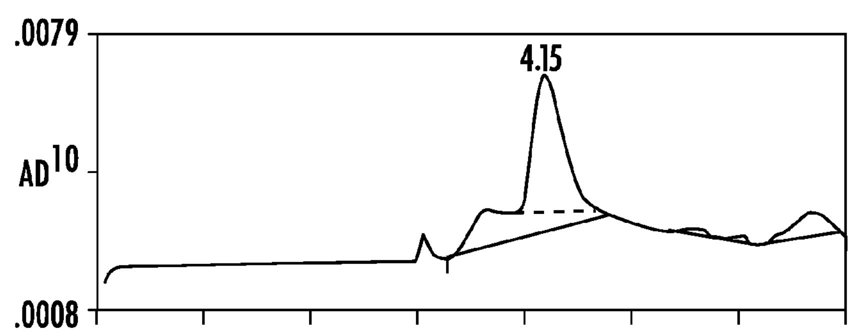
Figure 5:
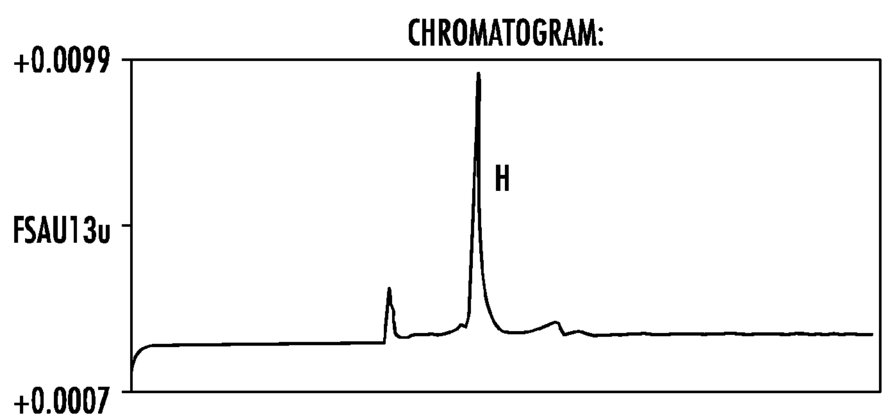

Two proteins are also precipitated in this method. Cryofibrinogen is similar to cryoglobulin in essence it is associated with same type of disorders nephropathy, neuropathy, purpura and thrombotic vasculopathy. It appears as relatively wide peak in the B2 region by CE, FIG. 5. In serum, it should be absent except in unusual occasions where the patient on anticoagulant therapy. It can be confirmed on immunodiffusion plate, by adding thrombin, or collecting another sample. It precipitates better by lowering the pH. This protein can be detected by immunoassay or perhaps by the use of an extra buffer.

EXAMPLE 10

Precipitation Quantification

Figure 6:
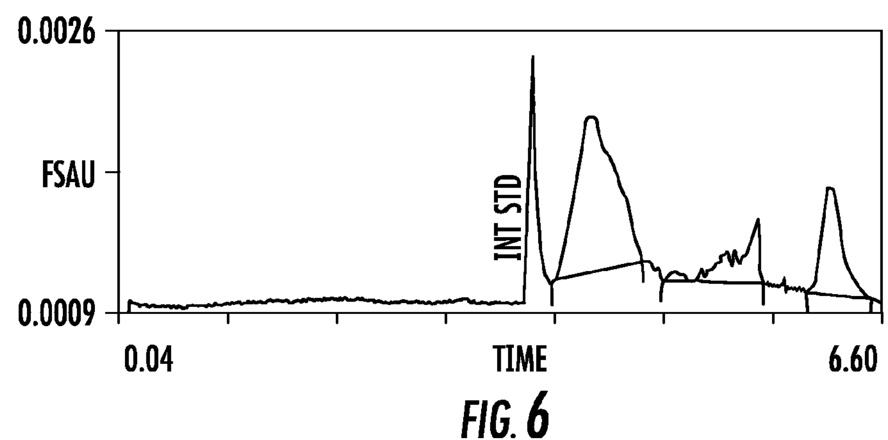
FIG. 6 shows an illustration for the internal standard on a Sebia gel system.

For calculation the peak of Triton X was used, FIG. 6, or lysozyme (for agarose) as internal standard after correcting for serum protein contamination based on the albumin content.

In brief, the method of the present invention improves the analysis of cryoglobulins. It is faster than the previous methods which relied on simple cooling. The precipitation occurs in terms of minutes compared to days, with fewer steps and with enhanced sensitivity. The precipitate is better solubilized due to the use of the special mixture which involves dissolving based on the following: Use special buffers, detergents, high pH and salts. Quantification by this method is more accurate since the cryoprecipitate is corrected for albumin co-precipitation and the addition of an internal standard detergent peak for the CE.

EXAMPLE 11

Sebia Agarose Gel

Figure 7:
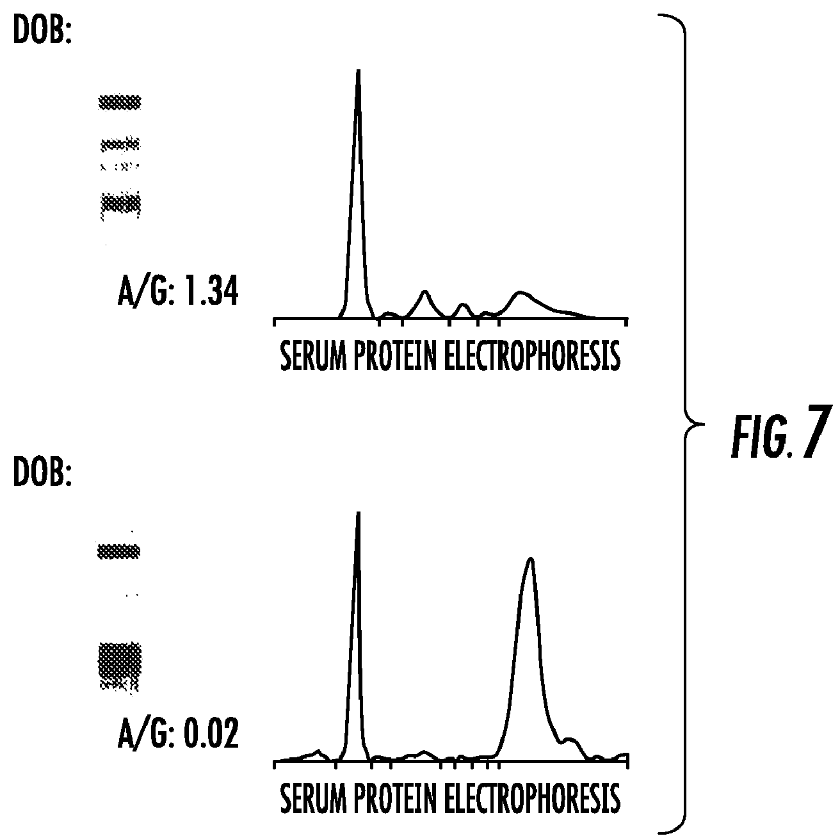
FIG. 7 provides an illustration of patient type III cryoglobulins determined with a sebia system (top=serum, bottom=cryoglobulin).

The system has not been completely optimized for the Sebia gel system. A few samples were run with a Beckman system. The method of the invention worked well because serum samples are diluted five times while the cryoglobulins can be applied directly. On example with a Sebia system is given in FIG. 7.

EXAMPLE 12

Role of Decreased Ionic Strength

Note that it is not the type of buffer but decreasing the ionic strength of the serum by dilution with a low ionic strength solution that is the key finding on which the instant invention is based. The buffer function in the reagent is to keep the precipitation consistent and reproducible. Phosphate ions are normally present in serum and this gives a more natural buffering system so for this reason it was chosen. However, the buffer is not necessary for the precipitation, and any other buffer or any ions can carry out this function.

Figure 8:
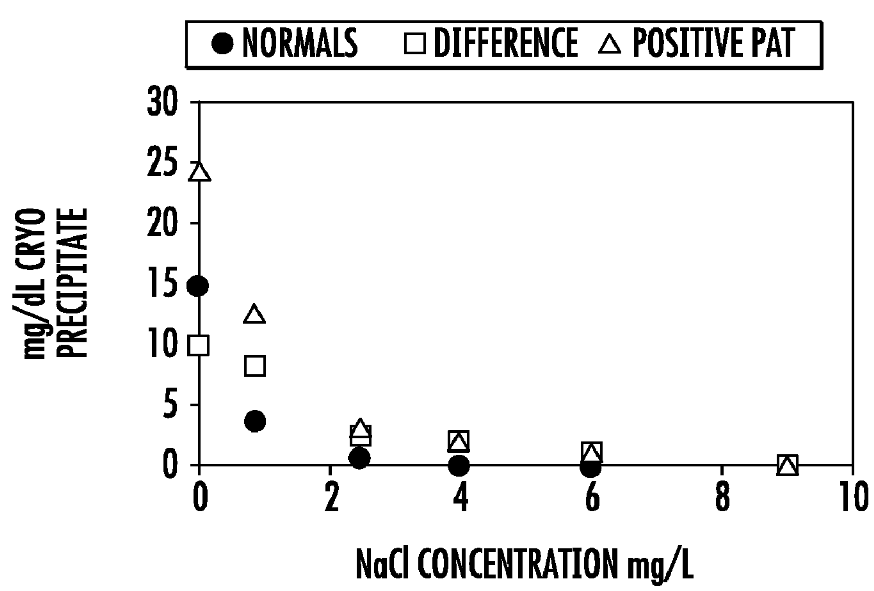
FIG. 8 shows the effect of low ionic strength as salt (NaCL) concentration at 0° C.

FIG. 8 shows the importance of decreasing the ionic strength of the serum. Precipitation occurs in the absence of the buffer just using different low concentrations of sodium ion or by dilution in pure water (the zero concentration). Pure water alone can bring along some precipitation, but it also precipitates the serum from the normal individuals. The described amount of sodium ions was chosen as giving a minimum amount of precipitation of serum from normal individuals but a maximum amount of precipitation for patients with cryoglobulin. Under the described conditions the precipitate of cryoglobulins from normal individuals is negligible. A different normal range can be constructed for dilution in pure water in a routine manner if desired.

The foregoing is illustrative of the present invention, and is not to be construed as limiting thereof. The invention is defined by the following claims, with equivalents of the claims to be included therein.

That which is claimed is:

1. A method for the precipitation of cryoglobulins, comprising the steps of:

(a) providing an aqueous cryoglobulin sample;

(b) providing a buffer reagent, said buffer reagent comprising sodium chloride in an amount of from 0 to 9 g/L;

(c) combining said cryoglobulin sample with said buffer reagent to decrease the ionic strength of the sample and produce a test sample; then (d) chilling said test sample at a temperature less than room temperature for a time of from 15 minutes to one hour to form a cryoglobulin precipitate in said test sample; and then, (e) within a time of not more than one hour, centrifuging said test sample to separate said cryoglobulin precipitate from said test sample, wherein said cryoglobulin precipitate is present in an amount sufficient to quantify and determine its type.

2. The method of claim 1, wherein said cryoglobulin sample is a human cryoglobulin sample.

3. The method of claim 1, wherein said cryoglobulin sample is a cryoglobulin type III sample.

4. The method of claim 1, wherein said cryoglobulin sample is a serum sample.

5. The method of claim 1, wherein said buffer reagent is a phosphate buffer reagent.

6. The method of claim 1, wherein said buffer reagent comprises 2.6 g/L NaCl.

7. The method of claim 1, wherein said buffer reagent comprises from 0 to 1.5 g/L $Na_2HPO_4$ and from 0 to 1 g/L $NaH_2PO_4$.

8. The method of claim 1, wherein said buffer reagent further comprises a preservative.

9. The method of claim 1, wherein said buffer reagent further comprises sodium azide.

10. A method for the precipitation of cryoglobulins, comprising the steps of:

(a) providing an aqueous cryoglobulin sample;

(b) providing a buffer reagent, said buffer reagent comprising sodium chloride in an amount of from 0 to 9 g/L;

(c) combining said cryoglobulin sample with said buffer reagent to decrease the ionic strength of the sample and produce a test sample; then (d) chilling said test sample at a temperature less than room temperature for a time of from 15 minutes to one hour to form a cryoglobulin precipitate in said test sample; and then (e) within a time of not more than one hour, centrifuging said test sample to separate said cryoglobulin precipitate from said test sample;

(f) solubilizing said cryoglobulin precipitate to form a dissolved precipitate, and then (g) analyzing said dissolved precipitate by electrophoresis to determine the quantity and type thereof.

11. The method of claim 1, wherein said buffer reagent comprises sodium chloride in an amount of from 1 to 6 g/L.

12. The method of claim 1, wherein said buffer reagent comprises sodium chloride in an amount of from 1 to 4 g/L.

13. A method for the precipitation of cryoglobulins, comprising the steps of:

(a) providing an aqueous cryoglobulin sample;

(b) combining said cryoglobulin sample with water or a buffer reagent to decrease the ionic strength of the sample and produce a test sample; then (c) chilling said test sample at a temperature less than room temperature for a time of from 15 minutes to one hour to form a cryoglobulin precipitate in said test sample; and then, (d) within a time of not more than one hour, centrifuging said test sample to separate said cryoglobulin precipitate from said test sample, wherein said cryoglobulin precipitate is present in an amount sufficient to quantify and determine its type.

14. The method of claim 13, wherein said cryoglobulin sample is a human cryoglobulin sample.

15. The method of claim 13, wherein said cryoglobulin sample is a cryoglobulin type III sample.

16. The method of claim 13, wherein said cryoglobulin sample is a serum sample.

17. The method of claim 13, wherein said buffer reagent is a phosphate buffer reagent.

18. The method of claim 10, wherein said buffer reagent is a phosphate buffer reagent.

19. The method of claim 10, wherein said buffer reagent comprises sodium chloride in an amount of from 1 to 6 g/L.

20. The method of claim 10, wherein said buffer reagent comprises sodium chloride in an amount of from 1 to 4 g/L.

* * * * *